(12) United States Patent
Palepu et al.

(10) Patent No.: US 6,727,280 B2
(45) Date of Patent: Apr. 27, 2004

(54) METHOD FOR TREATING COLORECTAL CARCINOMA USING A TAXANE/TOCOPHEROL FORMULATION

(75) Inventors: Nagesh Palepu, Mill Creek, WA (US); Dean Kessler, Edmonds, WA (US); Alexander K. Tustian, Mukilteo, WA (US); Steven C. Quay, Edmonds, WA (US); Panayiotis P. Constantinides, Gurnee, IL (US); Karel J. Lambert, Seattle, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 32 days.

(21) Appl. No.: 10/188,289

(22) Filed: Jul. 1, 2002

(65) Prior Publication Data

US 2003/0087953 A1 May 8, 2003

Related U.S. Application Data

(63) Continuation-in-part of application No. 09/317,499, filed on May 24, 1999, now Pat. No. 6,660,286, which is a continuation-in-part of application No. 09/003,173, filed on Jan. 5, 1998, now Pat. No. 6,458,373.
(60) Provisional application No. 60/048,480, filed on Jun. 6, 1997, and provisional application No. 60/034,188, filed on Jan. 7, 1997.

(51) Int. Cl.[7] ............... A61K 31/21; A61K 31/355; A61K 9/14; A61K 9/65; A01N 25/00
(52) U.S. Cl. ............... 514/511; 514/458; 424/405; 424/486; 424/455
(58) Field of Search ................ 514/511, 458; 424/405, 486, 455

(56) References Cited

U.S. PATENT DOCUMENTS

| 5,496,804 | A | 3/1996 | Reed et al. |
| 5,670,537 | A | 9/1997 | Canetta et al. |
| 5,681,846 | A | 10/1997 | Trissel |
| 5,733,526 | A | 3/1998 | Trevino et al. |
| 5,877,205 | A | 3/1999 | Andersson |
| 5,952,004 | A | 9/1999 | Rudnic et al. |
| 5,972,992 | A | 10/1999 | Carver et al. |
| 5,977,164 | A | 11/1999 | Carver et al. |
| 6,096,331 | A | 8/2000 | Desai et al. |
| 6,136,846 | A | 10/2000 | Rubinfeld et al. |
| 6,140,359 | A | 10/2000 | Carver et al. |
| 6,150,398 | A | 11/2000 | Vande Woude et al. |
| 6,319,943 | B1 | 11/2001 | Joshi et al. |
| 6,348,215 | B1 | 2/2002 | Straubinger et al. |
| 6,414,014 | B1 | 7/2002 | Canetta et al. |
| 6,506,405 | B1 | 1/2003 | Desai et al. |
| 6,509,370 | B1 | 1/2003 | Joshi-Hangal et al. |
| 6,537,579 | B1 | 3/2003 | Desai et al. |

FOREIGN PATENT DOCUMENTS

| EP | 0 427 582 A2 | 5/1991 |
| EP | 0 988 858 A1 | 3/2000 |
| WO | WO 95/11039 A1 | 4/1995 |
| WO | WO 95/20943 A1 | 8/1995 |
| WO | WO 95/31217 A1 | 11/1995 |
| WO | WO 96/22103 A1 | 7/1996 |
| WO | WO 97/03651 A1 | 2/1997 |
| WO | WO 98/30204 A1 | 2/1997 |
| WO | WO 98/30205 A1 | 7/1998 |
| WO | WO 99/04787 A1 | 2/1999 |
| WO | WO 00/50007 A1 | 8/2000 |
| WO | WO 00/71163 A1 | 11/2000 |
| WO | WO 01/22937 A1 | 4/2001 |

OTHER PUBLICATIONS

Eastman Vitamin E TPGS, *Properties and Applications*, Eastman Chemical Company Publication EFC–226, Oct. 1996.
Kelloff et al., "Clinical Development Plan: Vitamin E," *J. Cellular Biochem. Suppl.* 20:282–299, 1994.

*Primary Examiner*—Russell Travers
(74) *Attorney, Agent, or Firm*—Christensen O'Connor Johnson Kindness PLLC

(57) ABSTRACT

The present invention provides methods for administering a taxane composition for the treatment of cancer. In one aspect, the compositions are not diluted prior to administration. Some embodiments provide methods for administering a taxane as a bolus injection or an intravenous infusion in less than about 30 minutes. In other aspects, the invention provides methods for administering a taxane to provide high concentrations of the taxane in blood or in tumors. Another aspect provides methods for administering a taxane to provide anti-tumor activities against solid tumors. In some embodiments, the methods provide anti-tumor activities against tumors that were resistant to conventional taxane administration methods. In some embodiments, the methods provide anti-tumor activities against colorectal tumors.

42 Claims, 14 Drawing Sheets

| | | |
|---|---|---|
| Paclitaxel: | R= C_6H_5, | MW = 854 |
| 7-*epi*-paclitaxel: | C-7 : a-OH | |
| Cephalomannine: | R= *cis*-C_4H_7 | |
| *Iso*-Cephalomannine: | R= *cis*-C_4H_7, | C-7: a-OH |
| 10-Deacetyl-paclitaxel | C-10 : OH | |
| Baccatin III: | C-13 : OH | |

FIGURE 3

Table 1. Design of the B16 Melanoma Efficacy Study

| Group # | # of Mice | Paclitaxel Formulation | Paclitaxel Dosage (mg/kg) | Schedule |
|---|---|---|---|---|
| 1 | 8 | Saline | 0 (7 mL/kg) | q3dx5 |
| 2 | 8 | Vehicle | 0 (7 mL/kg) | q3dx5 |
| 3 | 8 | TAXOL | 20 | q3dx5 |
| 4 | 8 | QW8184 | 20 | q3dx5 |
| 5 | 8 | QW8184 | 40 | q3dx5 |
| 6 | 8 | QW8184 | 60 | q3dx5 |
| 7 | 8 | Vehicle | 0 (8 mL/kg) | q4dx5 |
| 8 | 8 | TAXOL | 20 | q4dx5 |
| 9 | 8 | QW8184 | 20 | q4dx5 |
| 10 | 8 | QW8184 | 50 | q4dx5 |
| 11 | 8 | QW8184 | 70 | q4dx5 |

FIGURE 6

Table 2. Comparative Anti-tumor Activities of Paclitaxel/Tocopherol (QW8184) and TAXOL in the B16 Melanoma Model

| Test Article | Dosage (mg/kg/day) | Schedule (days) | Median Tumor Volume on Day (post tumor implant) | | | | | | | | | | | | Survival Days (Mean ± SD) | % Mortality (by day 20) | % T/C Day 20 | T-C (days) |
|---|---|---|---|---|---|---|---|---|---|---|---|---|---|---|---|---|---|---|
| | | | 3 | 6 | 8 | 10 | 13 | 15 | 17 | 20 | 23 | 27 | 30 | 34 | | | | |
| Saline | 0 (7 mL/kg) | q3dx5 | 0 | 0 | 16 | 79 | 386 | 699 | 1361 | 2422 | | | | | 17 ± 2 | 87.5 | --- | --- |
| Vehicle | 0 (7 mL/kg) | q3dx5 | 0 | 3 | 22 | 26 | 246 | 388 | 689 | 2358 | | | | | 20 ± 1 | 0* | 97 | 3 |
| BMS Taxol | 20 | q3dx5 | 0 | 2 | 19 | 32 | 147 | 306 | 657 | 1871 | | | | | 19 ± 5 | 50 | 77 | 3 |
| QW8184 | 20 | q3dx5 | 0 | 11 | 19 | 8 | 28 | 50 | 159 | 270 | 903 | 1904 | 186 | 1340 | 28 ± 7 | 0 | 11 | 10 |
| QW8184 | 40 | q3dx5 | 0 | 4 | 10 | 1 | 9 | 7 | 10 | 6 | 139 | 352 | | | 33 ± 5 | 0** | 0 | 17 |
| QW8184 | 60 | q3dx5 | 0 | 0 | 5 | 4 | 7 | | | | | | | | 11 ± 3 | 100 | --- | --- |
| Vehicle | 0 (8 mL/kg) | q4dx5 | 0 | 7 | 20 | 38 | 194 | 400 | 1124 | 2658 | | | | | 16 ± 6 | 62.5 | 110 | 0 |
| BMS Taxol | 20 | q4dx5 | 0 | 5 | 13 | 12 | 80 | 184 | 321 | 1679 | | | | | 12 ± 7 | 75 | 69 | 3 |
| QW8184 | 20 | q4dx5 | 0 | 3 | 13 | 15 | 92 | 223 | 372 | 855 | 1079 | 2563 | | | 20 ± 3 | 50 | 35 | 3 |
| QW8184 | 50 | q4dx5 | 0 | 3 | 14 | 9 | 12 | 49 | 107 | 246 | 407 | 1001 | 1313 | | 31 ± 4 | 0 | 10 | 7 |
| QW8184 | 70 | q4dx5 | 0 | 0 | 3 | 4 | 3 | 2 | 0 | 2 | 15 | 64 | 122 | 1577 | 17 ± 16 | 62.5 | 0 | 17 |

* All Sacrificed due to excessive tumor size
** All animals survived to Day 27 when 3 were sacrificed due to tumor size (>10% of body weight)
% T/C = Tumor Growth Inhibition (median tumor wt. of treated/median tumor wt. control) x 100
T-C = Tumor Growth Delay value (median time for treatment group (T) and control group tumors (C) to reach a predetermined size (>750 mg)
Log cell kill = (T-C value)/(3.32 x tumor doubling time)

FIGURE 7

Table 3. Dosing Regimens for Paclitaxel Formulations in the HCT-15 Colon Tumor Xenograft Mouse Model

| Group | # of Mice | Test Formulation | Dosage (mg/kg) | Diluted Concentration (mg/mL) | Dose Vol. (mL/kg) | Schedule |
|---|---|---|---|---|---|---|
| 1 | 10 | Saline | 0 | 0 | 10 | q3dx5 |
| 2 | 10 | Vehicle | 0 | 0 | 10 | q3dx5 |
| 3 | 10 | S-8184 | 15 | 1.5 | 10 | q3dx5 |
| 4 | 10 | S-8184 | 30 | 1.5 | 20 | q3dx5 |
| 5 | 10 | S-8184 | 45 | 4.5 | 10 | q3dx5 |
| 6 | 10 | S-8184 | 60 | 6 | 10 | q3dx5 |
| 7 | 10 | TAXOL | 15 | 1.5 | 10 | q3dx5 |
| 8 | 10 | TAXOL | 30 | 1.5 | 20 | q3dx5 |
| 9 | 10 | TAXOL | 15 | 1.5 | 10 | qdx5 |
| 10 | 10 | S-8184 | 15 | 1.5 | 10 | qdx5 |

FIGURE 9

Table 4A. Summary of Pharmacokinetic Parameters of Paclitaxel Following TAXOL Administration in Humans (Mean Values)

| Dose (mg/m²) | Infusion Duration (h) | N (patients) | Cmax (ng/mL) | AUC$_{(0-\infty)}$ ng*h/mL) | T$_{1/2}$ (h) | CL$_T$ (L/h/m²) |
|---|---|---|---|---|---|---|
| 135 | 24 | 2 | 195 | 6300 | 52.7 | 21.7 |
| 175 | 24 | 4 | 365 | 7993 | 15.7 | 23.7 |
| 135 | 3 | 7 | 2170 | 7952 | 13.1 | 17.7 |
| 175 | 3 | 5 | 3650 | 15007 | 20.2 | 12.2 |

C$_{max}$ = Maximum plasma concentration
AUC$_{(0-\infty)}$ = Area under the plasma concentration-time curve from time 0 to infinity
CL$_T$ = Total body clearance Table 4B. Summary of Pharmacokinetic Parameters of Paclitaxel Following Paclitaxel/Tocopherol Administration (Mean Values)

| Dose (mg/m²) | N (patients) | C$_{max}$ (ng/mL) | AUC$_{(0-\infty)}$ ng*h/mL) | T$_{1/2}$ (h) | K$_e$ (h⁻¹) | CL$_T$ (L/h/m²) | MRT (h) | V$_{ss}$ (L/m²) |
|---|---|---|---|---|---|---|---|---|
| 175 | 10 | 67717 | 59813 | 21.5 | 0.0327 | 3.24 | 3.07 | 10.53 |
| 200 | 10 | 90917 | 84374 | 20.9 | 0.0335 | 2.74 | 2.73 | 7.57 |
| 225 | 10 | 84141 | 86368 | 19.7 | 0.0357 | 2.73 | 2.78 | 7.45 |

C$_{max}$ = Maximum blood concentration
AUC$_{(0-\infty)}$ = Area under the blood concentration-time curve from time 0 to infinity
CL$_T$ = Total body clearance
Ke = Elimination rate constant
MRT = Mean residence time
V$_{ss}$ = Volume of distribution at steady state FIGURE 11
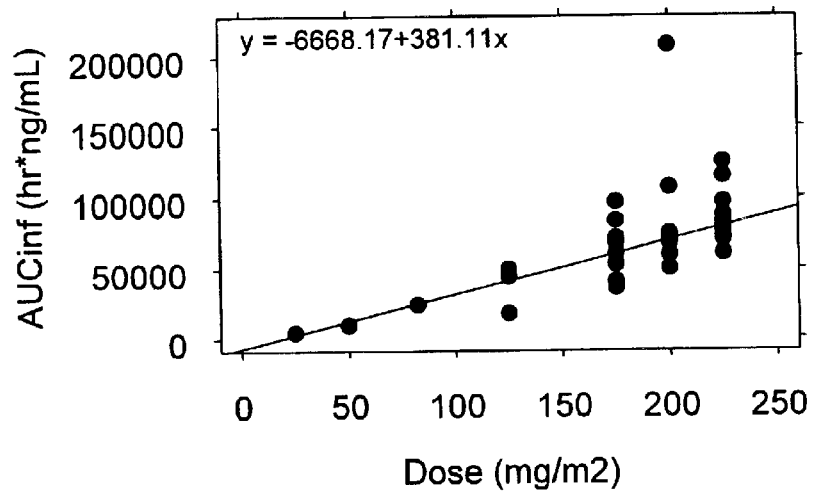
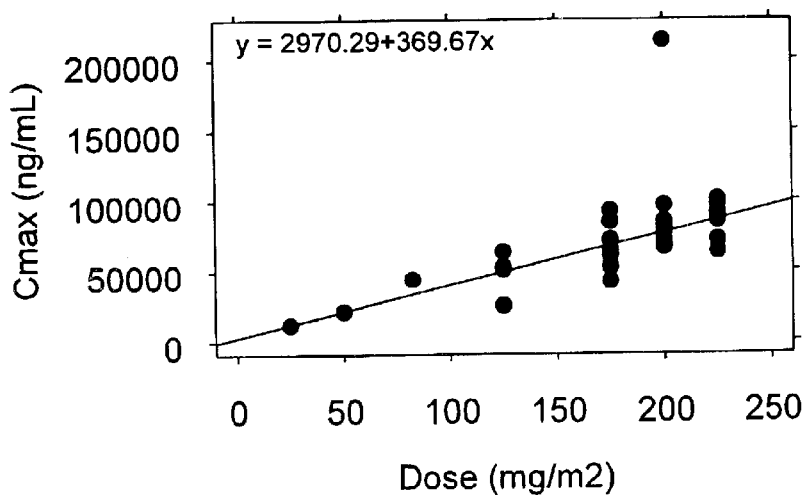

FIGURE 12

Table 5. Tumor Levels of Paclitaxel in Mice after Intravenous Administration of Paclitaxel/Tocopherol (S-8184) and TAXOL at 10 mg/kg (Mean ± S.E.M.; n=4 to 6)

| Tissue | Article | 0.5 hr | | 1 hr | | 4 hr | | 24 hr | | 48 hr | | 1 week | |
|---|---|---|---|---|---|---|---|---|---|---|---|---|---|
| Tumor ng/g | S-8184 | 2957 | ± 529 | 6080 | ± 1149 | 8164 | ± 3437 | 1258 | ± 413 | 409 | ± 195 | 8 | ± 6 |
| | TAXOL | 5018 | ± 891 | 5321 | ± 841 | 3133 | ± 515 | 681 | ± 159 | 167 | ± 46 | 12 | ± 6 |

Table 6. Calculated Pharmacokinetic Parameters of Paclitaxel in Mice after Administration of Paclitaxel/Tocopherol (S-8184) and TAXOL at 10 mg/kg.

| Tissue | Formulation | $C_{max}$ | $T_{1/2}$ | $AUC_{0-t}$ | $AUC_{0-t}$ Ratio of S-8184:Taxol | |
|---|---|---|---|---|---|---|
| Tumor | S-8184 | 8164 | 10.3 | 163.0 | | |
| | TAXOL | 5321 | 10.4 | 75.5 | 2.158 | (1.31 – 3.48) |

FIGURE 14

Table 7. Summary of Efficacy of Paclitaxel/Tocopherol in Ongoing Phase I Study

| Patient # | Current Dose mg/m² | Initial Dose mg/m² | Tumor Type | # Cycles on Study | Response/Comment | Prior Treatments |
|---|---|---|---|---|---|---|
| 9 | 175 | 175 | NSCLC | 12+ | Partial Response x 11+ months | TAXOL/carboplatin; GEMZAR/carboplatin; TAXOTERE/GEMZAR; TAXOTERE/NAVELBINE |
| 11 | 175 | 225 | Colorectal | 10+ | Partial Response x 9+ months | fluorouracil/leucovorin; irinotecan; XELODA; TEMODAR |
| 31 | 200 | 200 | Ovarian | 5+ | Partial Response x 3+ months | TAXOL/carboplatin |
| 13 | 225 | 225 | Ovarian | 5 | Minor Response | TAXOL/carboplatin x 2; topotecan; doxil |
| 10 | 175 | 175 | Breast | 4 | Minor response | fluorouracil/doxorubicin; tamoxifen; TAXOL; doxorubicin/cyclophosphamide; fluorouracil/ENILURACIL; HERCEPTIN x 2; NAVELBINE; ARIMIDEX |
| 15 | 225 | 225 | Mesothelioma | 7 | Stable Disease x 5 months | EPOTHILONE/doxorubicin; gemcitabine; gemcitabine/NAVELBINE; doxorubicin/carboplatin |
| 7 | 125 | 125 | NSCLC | 6 | Stable Disease x 5 months | TAXOL/carboplatin; TAXOTERE/NAVELBINE/gemcitabine; cisplatin/VP-16 |
| 19 | 100 | 175 | Breast | 4 | Stable Disease x 4 months | doxorubicin x 2; Stem cell transplant; TAXOL; ENILURACIL/fluorouracil; NAVELBINE |
| 16 | 175 | 225 | Ovarian | 5 | Stable Disease x 3 months | ifosfamide; topotecan; cisplatin |
| 8 | 175 | 175 | NSCLC | 4 | Stable Disease x 3 months | TAXOL/carboplatin; NAVELBINE/gemcitabine; cisplatin/VP-16; TAXOTERE |
| 33 | 200 | 200 | Colorectal | 4 | Stable Disease x 3+ months | fluorouracil/leucovorin; fluorouracil/leucovorin/CPT-11; XELODA |
| 28 | 225 | 225 | NSCLC | 5+ | Stable Disease x 3+ months | carboplatin/TAXOTERE; GEMZAR |
| 29 | 175 | 200 | Unknown primary | 5+ | Stable Disease x 3+ months | irinotecan/gemcitabine; TAXOL/carboplatin/gemcitabine |
| 35 | 200 | 200 | Colorectal | 3+ | Stable Disease x 2+ months | fluorouracil/leucovorin; CPT-11; XELODA |
| 37 | 175 | 200 | NSCLC | 3+ | Stable Disease x 2+ months | TAXOL/carboplatin/VP-16; NAVELBINE/GEMZAR/topotecan |

US 6,727,280 B2

METHOD FOR TREATING COLORECTAL CARCINOMA USING A TAXANE/TOCOPHEROL FORMULATION

CROSS-REFERENCES TO RELATED APPLICATIONS

This application is a continuation-in-part of U.S. application Ser. No. 09/317,499, filed May 24, 1999, now U.S. Pat. No. 6,660,286 which is a continuation-in-part of U.S. application Ser. No. 09/003,173, filed Jan. 5, 1998 now U.S. Pat. no. 6,458,373, each of which claims the benefit of U.S. Provisional Application No. 60/034,188, filed Jan. 7, 1997, and U.S. Provisional Application No. 60/048,480, filed Jun. 6, 1997. The benefit of the priority of the filing dates of these applications is hereby claimed under 35 U.S.C. §§119 and 120. Each of the above-noted applications is incorporated herein by reference in its entirety.

FIELD OF THE INVENTION

This invention relates to methods for administration of taxane/tocopherol formulations for the treatment of cancer.

BACKGROUND OF THE INVENTION

Paclitaxel is one of the most potent anticancer agents for the treatment of several cancers, including breast, ovarian, and lung cancers. Paclitaxel is a lipophilic molecule and is virtually insoluble in water. The poor aqueous solubility of paclitaxel has hindered the development of a suitable formulation for administration to patients.

The commercially available paclitaxel product, TAXOL (Bristol-Myers Squibb Oncology), is formulated in a vehicle containing an approximately 1:1 (v/v) mixture of polyoxyethylated castor oil (Cremophor EL) and ethanol. There are several disadvantages associated with the use of the TAXOL formulation of paclitaxel. Foremost among these is the presence of Cremophor EL in the formulation. Cremophor EL has been associated with bronchospasm, hypotension, and other manifestations of hypersensitivity, particular following rapid administration. As a result, the administration of TAXOL requires long infusion times of diluted material and premedication to reduce these adverse effects (Suffness, M. (1995), TAXOL Science and Applications, CRC Press). Typically, TAXOL is diluted about 10 to 20 fold prior to administration, and the approved infusion times range from 3 to 24 hours.

Several attempts have been made to provide paclitaxel formulations that overcome the problems associated with TAXOL. In one approach, the aqueous solubility of paclitaxel has been enhanced through the development of prodrugs, such as pegylated paclitaxel or polyglutamate paclitaxel. These compounds successfully increase the aqueous solubility of paclitaxel and thereby avoid the use of toxic solvents to solubilize paclitaxel. However, the pro-drugs require the presence of enzymes in the blood or tissue to cleave the water-soluble component of the pro-drug from the paclitaxel moiety. Therefore, the therapeutic utility of paclitaxel can be compromised if the level of activity of the enzyme required to release the paclitaxel from the pro-drug is low, as is frequently the case among the cancer patients. Generally, these pro-drugs are infused slowly to avoid adverse reactions.

Another approach has used human albumin coated paclitaxel nanoparticles to avoid the use of toxic solvents. However, the utility of these nanoparticles is limited by the slow dissociation of paclitaxel from the albumin coat.

Therefore, there remains a need in the art for paclitaxel formulations that overcome the disadvantages of prior art formulations. Moreover, there remains a need to identify a method for administrating paclitaxel that will reduce side effects and improve the therapeutic efficacy of paclitaxel.

SUMMARY OF THE INVENTION

The present invention provides methods for administration of taxane formulations.

In one aspect, the invention provides methods for administering taxanes without dilution and mixing of the taxane formulation with other excipients or carriers prior to administration. In some embodiments, the invention provides methods for administering a taxane as a bolus injection. In some embodiments, the invention provides methods for administering a taxane as an intravenous infusion in less than about 30 minutes. In some embodiments, the invention provides methods for administering a taxane using only antihistamine premedication.

In another aspect, the invention provides methods for administering taxanes to deliver high concentrations of paclitaxel in blood. In some embodiments, the invention provides methods for administering taxanes to deliver mean peak blood concentrations of taxanes of greater than about 4,000 ng/mL after administration of a taxane dose of 175 mg/m$^2$. Some embodiments provide methods for administration that provide a mean extrapolated area-under-the-curve (AUC) concentration of taxanes in blood of greater than about 16,000 ng*h/mL after administration of a taxane dose of 175 mg/m$^2$. In some embodiments, the methods of the invention result in a mean total body clearance of the taxanes of less than about 11 L/h/m$^2$.

In another aspect, the invention provides methods for administering taxanes to deliver high concentrations of taxanes in tumors. In some embodiments, the invention provides methods for administering taxanes to provide a mean peak taxane concentration in tumors of more than 6000 ng/g of tumor mass after administration of a taxane dose of 10 mg/kg. In further embodiments, the invention provides methods for administering taxanes to provide a mean area-under-the-curve $(AUC)_{0 \rightarrow t}$ concentration of taxanes in tumors of more than 80 µg*h/g of tumor mass after administration of a dose of 10 mg/kg.

In another aspect, the invention provides methods for administering taxanes to obtain increased anti-tumor activities compared to TAXOL. In some embodiments, the invention provides methods for administering taxanes that are effective against taxane-resistant tumors.

In another aspect, the invention provides methods for treating subjects suffering from tumors. In some embodiments, the invention provides methods for treating subjects suffering from colorectal adenocarcinoma. In some embodiments, the invention provides methods for treating subjects suffering from carcinomas such as breast carcinoma, lung carcinoma, skin carcinoma, gastrointestinal carcinoma, ovarian carcinoma, and uterine carcinoma.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 shows Table 1 describing the design of the B16 melanoma study comparing the efficacy of TAXOL and paclitaxel/tocopherol (QW8184, also known as S-8184).

FIG. 6 shows Table 2 comparing the anti-tumor activities of paclitaxel/tocopherol (QW8184) and TAXOL in a murine B16 melanoma xenograft model.

FIG. 7 shows Table 3 describing various dosing regimes of paclitaxel/tocopherol (S-8184) and TAXOL in a HCT-15 colon tumor xenograft studies in nude mice.

FIG. 9 shows Tables 4A and 4B. Table 4A summarizes the human pharmacokinetic parameters of paclitaxel following TAXOL administration, and Table 4B summarizes the pharmacokinetic parameters of paclitaxel following administration of paclitaxel/tocopherol.

FIG. 11 shows that both AUC and $C_{max}$ are linearly related to the administered dose of paclitaxel/tocopherol.

FIG. 12 shows Tables 5 and 6 describing the tumor levels of paclitaxel in mice, and the calculated pharmacokinetic parameters for paclitaxel in tumors, after intravenous administration of paclitaxel/tocopherol (S-8184) and TAXOL at 10 mg/kg (Mean±S.E.M.; n=4 to 6), respectively.

FIG. 14 shows Table 7 summarizing the preliminary results from an ongoing paclitaxel/tocopherol Phase I clinical study in patients with refractory cancer. Different prior treatments are separated by semicolons. The minor response in Patient 13 included: a greater than 50% lymph node reduction×2 months and a greater than 50% decrease in cancer antigen-125×4 months. The minor response in Patient 10 included pleural effusion disappearance and decreased skin nodules. NSCLC=Non-small cell lung cancer.

DETAILED DESCRIPTION OF THE PREFERRED EMBODIMENT

The present invention provides methods for administration of taxane formulations. In one aspect, the methods of the invention (1) do not require dilution or mixing of the taxane formulation with excipients or other carriers prior to administration, (2) permit intravenous administration in less than 30 minutes, and (3) usually do not require premedications other than anti-histamines.

In another aspect, the invention provides methods for administration of taxanes to (1) deliver a higher peak blood concentration of taxanes than administration of TAXOL (e.g., at least a 18-fold higher), (2) provide a higher area-under-the-curve concentration of taxanes in blood than administration of TAXOL (e.g., at least a 4-fold higher), and (3) provide a lower clearance of taxanes from blood than administration of TAXOL (e.g., at least a 4-fold lower).

A further aspect of the invention provides methods for administration of taxanes to (1) deliver a higher taxane concentration in tumors than administration of TAXOL, and (2) provide a higher area-under-the-curve concentration of taxanes in tumors than administration of TAXOL.

Another aspect of the invention provides methods for administering taxanes that result in increased anti-tumor activities than similar dosages of TAXOL. In some embodiments, the methods for administration are effective against taxane-resistant tumors.

In yet another aspect, the invention provides methods for treating subjects suffering from tumors. Some embodiments provide methods for treating subjects suffering from colorectal adenocarcinoma.

Figure 1A:
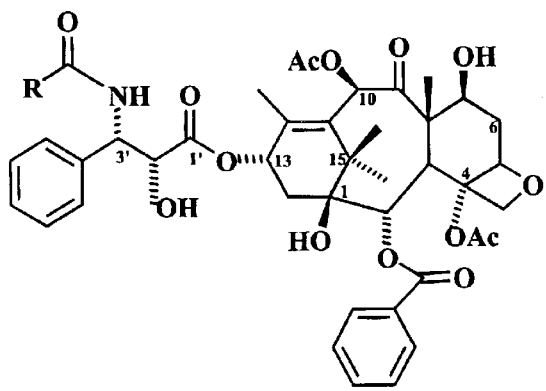
FIGS. 1A and 1B show the structure of paclitaxel and analogs, and the structure of the taxoid nucleus, respectively.

As used herein, the following terms have the meanings defined below:

Paclitaxel is a member of the taxane dipterine family and its analogs. The structure of the paclitaxel and several analogs is shown in FIG. 1A. Paclitaxel has a molecular formula of $C_{47}H_{51}NO_{14}$ and a molecular weight of 853.93. Paclitaxel can be prepared by extraction from the bark and needles of the Yew tree (*Taxus yunnanensis*). Alternatively, paclitaxel is prepared synthetically or semi-synthetically. Some embodiments include paclitaxel derivatives, for example benzoate derivatives of paclitaxel such as 2-debenzoyl-2-aroyl and C-2-acetoxy-C-4-benzoate paclitaxel, 7-deoxytaxol, C-4 aziridine paclitaxel, as well as various paclitaxel conjugates with natural and synthetic polymers, particularly with fatty acids, phospholipids, and glycerides and 1,2-diacyloxypropane-3-amine. As used herein, the term "paclitaxel" refers to paclitaxel, a paclitaxel derivative, or a paclitaxel analog.

Figure 1B:
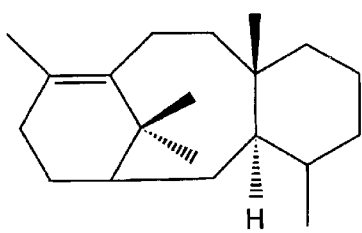

Other members of the family of related molecules called taxoids, taxanes, or taxines are also within the scope of the present invention. The structure of the taxoid nucleus is shown in FIG. 1B. The taxane can be any anti-mitotic taxane, taxane derivative or analog. It is generally believed that the mechanism of action of taxanes involves promoting formation and hyperstabilization of microtubules, thus blocking cell division. As used herein, the term "taxane" refers to a taxanes, taxines, and taxoids, as well as derivatives or analogs thereof.

In some embodiments, the taxane, taxane derivative, or taxane analog can include, for example, docetaxel (TAXOTERE, Aventis Pharmaceuticals); spicatin; taxane-2, 13-dione, 5β,9β,10β-trihydroxy-, cyclic 9,10-acetal with acetone, acetate; taxane-2,13-dione, 5β,9β,10β-trihydroxy-, cyclic 9,10-acetal with acetone; taxane-2β,5β,9β,10β-tetrol, cyclic 9,10-acetal with acetone; taxane; cephalomannine-7-xyloside; 7-epi-10-deacetylcephalomannine; 10-deacetylcephalomannine; cephalomannine; taxol B; 13-(2',3'-dihydroxy-3'phenylpropionyl)baccatin III; yunnanxol; 7-(4-azidobenzoyl)baccatin III; N-debenzoyltaxol A; O-acetylbaccatin IV; 7-(triethylsilyl)baccatin III; 7,10-di-O-[(2,2,2,-trichloroethoxy)carbonyl]baccatin III; baccatin III 13-O-acetate; baccatin diacetate; baccatin; baccatin VII; baccatin VI; baccatin IV; 7-epi-baccatin III; baccatin V; baccatin I; baccatin III; baccatin A; 10-deacetyl-7-epitaxol; epitaxol; 10-deacetyltaxol C; 7-xylosyl-10-deacetyltaxol; 10-deacetyltaxol-7-xyloside; 7-epi-10-deacetyltaxol;

10-deactyltaxol; or 10-deactyltaxol B, as well as any combination of two or more of the foregoing molecules.

Figure 2:
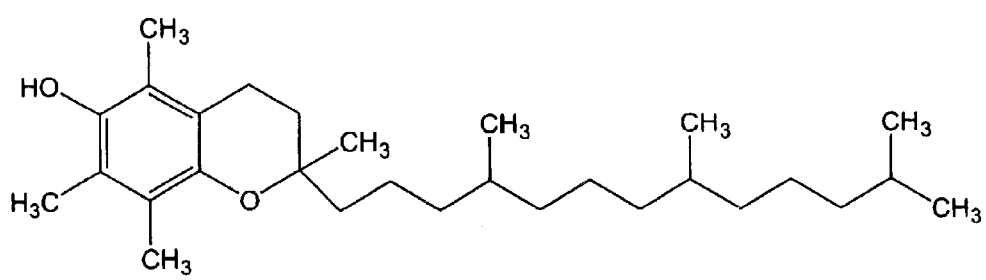
FIG. 2 shows the structure of a-tocopherol.

Tocopherols are a family of natural and synthetic compounds, also known by the generic names tocols or vitamin E. Among the tocopherols, a-tocopherol is the most abundant and active form of this class of compounds and it has the structure shown in FIG. 2. Other members of this class include α-, β-, γ-, and δ-tocotrienols, and α-tocopherol derivatives such as tocopherol acetate, phosphate, succinate, nitotinate and linoleate. As used herein, the term "tocopherol" refers to any member of the tocopherol family.

The term "taxane/tocopherol" refers to a pharmaceutical compositions comprising at least one taxane and at least one tocopherol. The term "paclitaxel/tocopherol" refers to a pharmaceutical composition comprising at least one paclitaxel and at least one tocopherol.

The term "tocopherol vehicle" refers to a paclitaxel/tocopherol composition without paclitaxel.

"TPGS" refers to d-a-tocopherol polyethylene glycol 1000 succinate (MW=~1513). TPGS is a vitamin E derivative in which polyethylene glycol subunits are attached by a succinic acid ester at the ring hydroxyl of the vitamin E molecule. TPGS is a non-ionic surfactant (HLB=16–18). Various chemical derivatives of vitamin E TPGS including ester and ether linkages of various chemical moieties are included within the definition of vitamin E TPGS. TPGS is reported to inhibit P-glycoprotein, a protein that contributes to the development of multi-drug resistance. In some embodiments, the diester content of TPGS in the formulations of the invention does not exceed 20%, and the free polyethylene glycol does not exceed 10% (w/w).

"Polyethylene glycol" (PEG) is a hydrophilic, polymerized form of ethylene glycol, consisting of repeating units of the chemical structure: (—$CH_2$—$CH_2$—O—). The general formula for polyethylene glycol is $H(OCH_2CH_2)_nOH$. The molecular weight ranges from 200 to 10,000. Such various forms are described as PEG-200, PEG-400, and the like. In a preferred embodiment, the therapeutic agents of the compositions of the invention can initially be solubilized in non-volatile co-solvents such as dimethylsulfoxide (DMSO), dimethylamide (DMA), propylene glycol (PG), polyethylene glycol (PEG), N-methyl-2-pyrrolidone (NMP) and polyvinylpyrrolidone (PVP); NMP or a water-soluble polymer such as PEG or PVP are particularly preferred.

A major advantage/improvement of using PEG-400 to solubilize therapeutic agents rather than alcohols such as ethanol is that a volatile solvent does not have to be removed- or diluted prior to administration of the therapeutic agent. The final polyethylene glycol levels in the emulsion can be varied from about 1 to about 50% (w/w), for example from about 1 to about 25%, or from about and more preferably from about 1 to about 10%. Suitable polyethylene glycol solvents are those with an average molecular weight between 200 and 600, preferably 300 and 400. In the case of self-emulsified systems for oral administration, high molecular weight PEGs (1,000–10,000) can also be included as solidification agents to form semi-solid formulations which can be filled into hard gelatin capsules.

"Poloxamers" or "pluronics" are synthetic block copolymers of ethylene oxide and propylene oxide having the general structure: $H(OCH_2CH_2)_a(OCH_2CH_2CH_2)_b(OCH_2CH_2)_aOH$. The following variants based on the values of a and b are commercially available from BASF Performance Chemicals (Parsippany, N.J.) under the trade name Pluronic and which consist of the group of surfactants designated by the CTFA name of poloxamer 108, 188, 217, 237, 238, 288, 338, 407, 101, 105, 122, 123, 124, 181, 182, 183, 184, 212, 231,282, 331,401,402, 185,215, 234,235,284, 333, 334, 335, and 403. For the most commonly used poloxamers 124, 188, 237, 338, and 407 the values of a and b are 12/20, 79/28, 64/37, 141/44 and 101/56, respectively.

The term "emulsion" refers to a colloidal dispersion of two immiscible liquids in the form of droplets, whose diameter, in general, are between 0.1 and 3.0 microns and which is typically optically opaque, unless the dispersed and continuous phases are refractive index matched. Such systems possess a finite stability, generally defined by the application or relevant reference system, which may be enhanced by the addition of amphiphilic molecules or viscosity enhancers.

The term "microemulsion" refers to a thermodynamically stable isotropically clear dispersion of two immiscible liquids, such as oil and water, stabilized by an interfacial film of surfactant molecules. The microemulsion has a mean droplet diameter of less than 200 nm, in general between 10–50 nm. In the absence of water, mixtures of oil(s) and non-ionic surfactant(s) form clear and isotropic solutions that are known as self-emulsifying drug delivery systems (SEDDS) and have successfully been used to improve lipophilic drug dissolution and oral absorption.

The term "biocompatible" means capable of performing functions within or upon a living organism in an acceptable manner, without undue toxicity or physiological or pharmacological effects.

The terms "bolus injection" or "slow intravenous push" or "IV push" refer to the intravenous administration of a taxane over a time period from about 5 to about 10 minutes.

The term "therapeutically effective amount" refers to an optimized amount of taxane/tocopherol such that the desired antitumor activity is provided without significant side-effects. The amount of a given drug that will be effective in the treatment of a particular tumor will depend in part on the severity of the tumor, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well-known factors, including route of administration, and the age, body weight, sex and general health of the individual; the nature, severity and clinical stage of the tumor(s); and the use (or not) of concomitant therapies. Of course, the skilled person will realize that divided and partial doses are also within the scope of the invention. For example, it may be appropriate to administer a weekly dose of about 80 mg/m$^2$ as a twice weekly dose of about 40 mg/m$^2$.

The term "$C_{max}$" refers to the peak or maximum concentration of a taxane in a defined body compartment (e.g., blood, plasma or serum).

The term "area-under-the-curve" or "AUC" refers to the integral of taxane concentration in a defined body compartment (e.g., blood, plasma or serum) over time, from zero to infinity or any interim time point. Thus, $AUC_{0-t}$ is the non-extrapolated area under the concentration-time curve from time 0 to a defined time point t, and $AUC_{0-\infty}$ is the extrapolated area under the concentration-time curve from time 0 to infinity.

The term "elimination half-life" refers to the time necessary to reduce the drug concentration in a specific compartment (e.g., blood, plasma or serum) by 50% after equilibrium is reached. The term "elimination rate constant" refers to the fraction of drug eliminated per unit of time. With first-order elimination, the rate of elimination is directly proportional to the serum drug concentration. There is a linear relationship between rate of elimination and serum drug concentration. Although the amount of drug eliminated in a first-order process changes with concentration, the fraction of a drug eliminated remains constant.

The term "clearance" refers to a measure of the body's ability to eliminate drug and is a hypothetical volume of distribution of drug which is cleared per unit time (i.e., mL/min) by any pathway of drug removal. It is important to clarify that the clearance does not indicate how much drug is being removed, rather, the volume of biological fluid such as blood or plasma that would have to be completely freed of drug to account for the elimination.

The term "volume of distribution" refers to a calculated volume of body fluid that would be required to dissolve the total amount of drug at the same concentration as that found in the blood. It is a proportionality constant relating the amount of drug in the body to the measured concentration in biological fluid (blood, plasma, serum).

The term "taxane-resistant tumor" or "taxane-refractory tumor" refers to a tumor that has not responded to prior art taxane treatment methods.

The term "anti-tumor activity" refers to the efficacy of a taxane composition in providing a therapeutic benefit to a subjects suffering from a tumor. The responses to treatment in solid tumors are evaluated using guidelines such as those published by the World Health Organization in 1979 (WHO handbook for reporting results of cancer treatment (1979), World Health Organization Offset Publication No. 48); by Miller et al. in 1981 (Miller et al. (1981) *Cancer* 47:207–214); and the response evaluation criteria in solid tumors (RECIST) by Therasse et al. in 2000 (Therasse et al. (2000) *J. Natl. Cancer Inst.* 92:205–216). For example, according to the RECIST criteria, a complete response is defined as the disappearance of all target lesions, a partial response is defined as at least a 30% decrease in the sum of the longest diameter of target lesions, progressive disease is defined as at least a 20% increase in the sum of the longest diameter of target lesions or the appearance of new lesions, and stable disease is defined as neither sufficient shrinkage to qualify for partial response nor sufficient increase to qualify for progressive disease. Thus, a complete or a partial response and stable disease represent the presence of anti-tumor activity, and progressive disease represents the absence of anti-tumor activity. Other evidence of anti-tumor activity is provided by, for example, when the administration of taxane reduces the overall tumor burden, results in an objective response, slows tumor progression, prevents tumor recurrence, prevents the appearance of new tumor lesions, results in a partial or complete response in a tumor lesion, or results in a therapeutic benefit to the subject.

In one aspect the invention provides methods for administering a pharmaceutical composition comprising at least one tocopherol and at least one taxane. In some embodiments, the taxane is paclitaxel. In some embodiments, the tocopherol is d,l α-tocopherol. Some embodiments of the invention provide methods for administering paclitaxel in an oil-in-water emulsion with the following composition:

| Component | Amount per mL |
|---|---|
| Paclitaxel | 5–20 mg |
| d,l α-Tocopherol (Vitamin E) | 20–100 mg |
| d-α-Tocopherol Polyethylene Glycol 1000 Succinate (TPGS) | 2–100 mg |
| Poloxamer 407 (Pluronic F127) | 5–20 mg |
| Polyethylene Glycol 400 (PEG 400) | 40–80 mg |
| Water for Injection | q.s. |

In a preferred embodiment, the emulsion comprises about 10 mg/mL paclitaxel, about 80 mg/mL tocopherol, about 50 mg/mL TPGS, about 10 mg/mL poloxamer 407, about 60 mg/mL PEG 400. In some embodiments, the emulsion incorporates paclitaxel at a nominal concentration of about 10 mg/L, as shown in EXAMPLES 5–7. In some embodiments, the paclitaxel concentration is between about 6 mg/mL to about 10 mg/mL. In some embodiments, the taxane concentration is more than 10 mg/ml. Some embodiments of the invention provide methods for administering a ready-to-use taxane/tocopherol formulation that requires no dilution or mixing with excipients or other carriers prior to administration, as shown in EXAMPLES 1–7. As used herein, the designations "QW8184" and "S-8184" refer to representative paclitaxel/tocopherol compositions.

In some embodiments, the dose of taxane administered is between about 15 and about 225 mg/m$^2$, as shown in EXAMPLES 6 and 7. Some embodiments provide for administration of a taxane at doses between about 25 and about 225 mg/m$^2$, as shown in EXAMPLE 5. Some embodiments provide for administration of a taxane at doses between about 175 and about 225 mg/m$^2$, as shown in EXAMPLE 3. Some embodiments provide for administration of a taxane at doses between about 60 and about 120 mg/m$^2$.

Some embodiments provide methods for administering a taxane to animals or humans via intravascular, oral, intramuscular, cutaneous and subcutaneous routes. Specifically, a taxane composition can be given by any of the following routes, among others: intraabdominal, intraarterial, intraarticular, intracapsular, intracervical, intracranial, intraductal, intradural, intralesional, intralumbar, intramural, intraocular, intraoperative, intraparietal, intraperitoneal, intrapleural, intrapulmonary, intraspinal, intrathoracic, intratracheal, intratympanic, intrauterine, and intraventricular. The emulsions of the present invention can be nebulized using suitable aerosol propellants that are known in the art for pulmonary delivery of lipophilic compounds.

In some embodiments, the taxane/tocopherol is administered by a bolus injection or by a slow intravenous push, as shown in EXAMPLES 1–7. In some embodiments, the taxane composition is administered intravenously over a period of less than about 60 minutes. In some embodiments, the taxane is administered intravenously over a period of less than about 30 minutes. In some embodiments, the taxane is administered intravenously over a period of less than about 15 minutes. In some embodiments, the formulation is administered intravenously over about 5 to about 10 minutes. In some embodiments, the invention provides methods for administering higher doses of taxane without resulting in severe toxicity compared to TAXOL, as shown in EXAMPLE 1. In some embodiments, the taxane is administered without pre-medications other than antihistamines, as shown in EXAMPLES 3 and 5–7.

In some embodiments, the administration cycles are once every three weeks, as shown in EXAMPLE 5. In yet further embodiments, the taxane is administered once every two weeks, weekly, twice weekly, or daily taxane, as shown in EXAMPLES 6 and 7.

Another aspect of the invention provides methods of the invention provide a high peak concentration ($C_{max}$) of the administered taxane in blood, as shown in EXAMPLE 3. In some embodiments, the peak blood concentration after taxane administration according to the invention is at least about 18-fold higher than the peak blood concentration of paclitaxel after administration of TAXOL, as shown in EXAMPLE 3.

Some embodiments provide an at least about 4-fold higher extrapolated area-under-the-curve concentration of the taxane in blood than that observed after administration of TAXOL, as shown in EXAMPLE 3. Some embodiments provide an at least about 4-fold slower clearance of taxane from blood than the clearance of paclitaxel after administration of TAXOL, as shown in EXAMPLE 3.

Another aspect of the invention provides methods for providing high concentrations of taxanes in tumors. In some embodiments, the peak tumor concentration ($C_{max}$) after taxane administration is at least about 2-fold higher than that obtained after administration of TAXOL, as shown in EXAMPLE 4. Some embodiments provide an at least about 2-fold higher area-under-the-curve concentration of taxane in tumors than that observed after administration of TAXOL, as shown in EXAMPLE 4.

In another aspect, the invention provides methods for administering a taxane to obtain increased anti-tumor activities compared to TAXOL, as shown in EXAMPLES 1, 2, and 5–7. Some embodiments provide methods for administering taxane formulations to subjects suffering from carcinomas, such as breast carcinoma, lung carcinoma, skin carcinoma, gastrointestinal carcinoma, ovarian carcinoma or uterus carcinoma, as shown in EXAMPLES 1, 2, and 5–7. In some embodiments, the invention provides methods for administering paclitaxel that are effective against taxane-resistant tumors, as shown in EXAMPLE 5. Some embodiments provide methods for administering taxane formulations to subjects suffering from colorectal adenocarcinomas, as shown in EXAMPLES 2 and 6.

Another aspect of the invention provides methods for treating subjects suffering from tumors. In some embodiments, the invention provides methods for treating subjects suffering from colorectal adenocarcinomas. Some embodiments provide methods for treating tumors that are resistant to prior art methods for taxane administration, as shown in EXAMPLES 2 and 5. Some embodiments provide methods for treating subjects suffering from colorectal adenocarcinoma, as shown in EXAMPLES 2, 5 and 6.

The following examples are provided for the purposes of illustrating, but not limiting, the present invention.

EXAMPLES

Example 1

Efficacy of Taxane/Tocopherol in Mouse B16 Melanoma Xenograft Model

This example shows the comparative efficacy of TAXOL and a representative paclitaxel/tocopherol composition on B16 melanoma xenografts in mice following two different schedules of administration.

Female B6D2F mice were subcutaneously implanted with $10^7$ B16 melanoma tumor cells. Four days after implantation, mice were randomly sorted into treatment groups and were intravenously administered saline, tocopherol vehicle, paclitaxel/tocopherol emulsion (QW8184) or TAXOL on a schedule of either q3dx5 (one dose every three days, repeated five times) or q4dx5 (one dose every four days, repeated 5 times). Paclitaxel/tocopherol was administered as a bolus injection and TAXOL was infused over 2 minutes following 10-fold dilution with saline (per the package insert). Table I in FIG. 3 lists the groups, dosages and schedules investigated in the study.

Results of the study indicate improved efficacy with paclitaxel/tocopherol in this model with both dosage schedules with regard to reduction in tumor size and mean survival time. In addition, paclitaxel/tocopherol illustrated a definitive dose response with both schedules.

Figure 4:
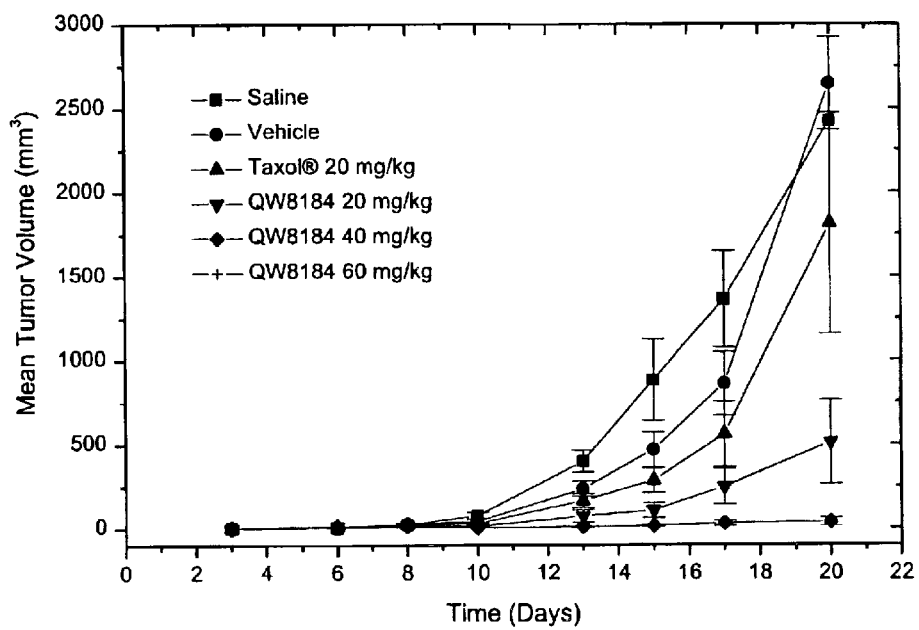
FIG. 4 compares the relative efficacy of TAXOL and paclitaxel/tocopherol on tumor growth following administration (q3dx5, one dose every three days, repeated five times) of paclitaxel/tocopherol (QW8184) and TAXOL (mean±S.E.M.). Note that the 60 mg/kg data are superimposed on the 40 mg/kg data in this figure.
Figure 5:
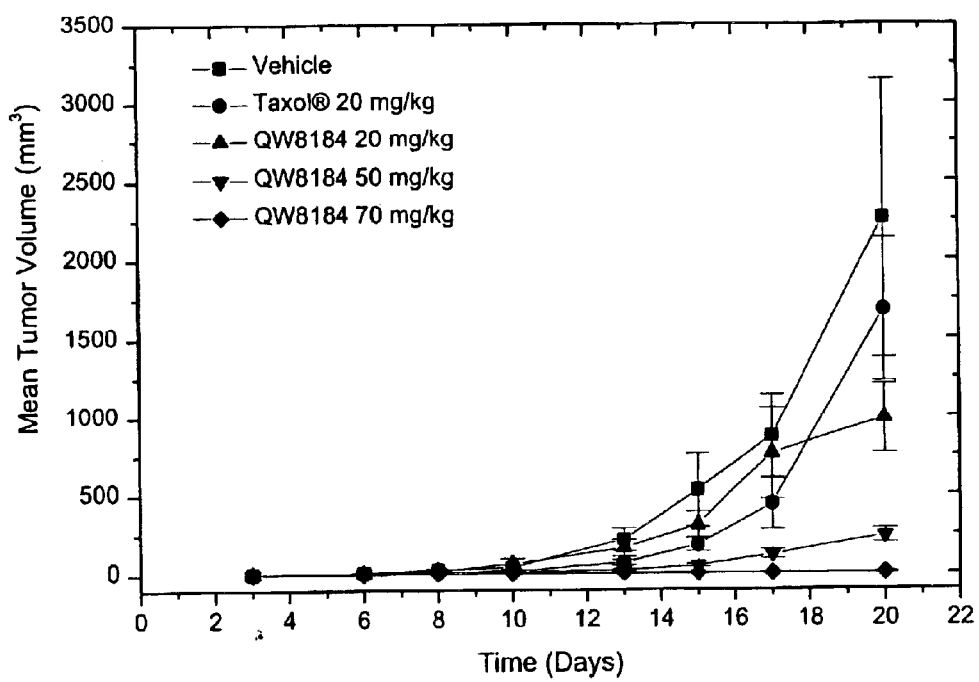
FIG. 5 shows tumor growth curves following administration (q4dx5, one dose every four days, repeated five times) of paclitaxel/tocopherol (QW8184) and TAXOL (mean±S.E.M.).

Intravenous administration of paclitaxel/tocopherol at dosages of 20 mg paclitaxel/kg (63 mg/m$^2$) and 40 mg paclitaxel/kg (125 mg/m$^2$) on a schedule of q3dx5 resulted in mean increases in survival times of 69% and 97%, respectively, as compared to the control group. Tumor growth was also reduced with paclitaxel/tocopherol as graphically depicted in FIG. 4. Note that the 60 mg/kg paclitaxel/tocopherol data are superimposed on the 40 mg/ml paclitaxel/tocopherol data in this figure. Log-cell kill values of 1.8 and 3.0 were observed with paclitaxel/tocopherol (q3dx5) at dosages of 20 and 40 mg paclitaxel/kg, respectively, while a log-cell kill value of 0.5 was observed with TAXOL at a dosage of 20 mg paclitaxel/kg (q3dx5). There was also a dramatic reduction in tumor growth in animals administered paclitaxel/tocopherol on a scheduled of q4dx5 as illustrated in FIG. 5. Table 2 in FIG. 6 lists the overall results of the study including mean survival times, median tumor weights and log cell kills for each group and treatment schedule.

Paclitaxel/tocopherol administration also had higher efficacy than TAXOL in nude mice implanted with IGROV-1 human ovarian tumor xenografts (see U.S. patent application Ser. No. 09/317,495, Table 20, hereby incorporated by reference). Paclitaxel/tocopherol was highly active against the IGROV-1 human ovarian xenografts in a dose-dependent fashion, regardless of the dosing schedule. The greatest number of complete responses with no toxic deaths were observed after administration of paclitaxel/tocopherol on a q4dx5 schedule. Administration of paclitaxel/tocopherol at a dosage of 20 mg paclitaxel/kg (120 mg/m$^2$) on a qdx5 schedule was well tolerated with no toxic deaths or substantial weight loss. In comparison, six toxic deaths were noted in mice administered TAXOL on this schedule.

Example 2

Efficacy of Taxane/Tocopherol in HCT-15 Xenograft Model

This example compares the efficacy of a representative paclitaxel/tocopherol composition and TAXOL in the a mouse HCT-15 xenograft model.

The human colon cancer cell line HCT-15 is resistant to the currently marketed paclitaxel products (TAXOL and TAXOTERE). Xenograft studies of HCT-15 tumors in mice were conducted to test whether the paclitaxel/tocopherol formulation would be effective against colorectal cancer. Approximately 107 cultured HCT-15 human colon tumor cells were implanted subcutaneously in nude mice. When tumors were approximately 100 mm$^2$ in size, the animals were divided into treatment and control groups and administered paclitaxel formulations as shown in Table 3 in FIG.

7. Paclitaxel/tocopherol was administered as a bolus injection and TAXOL was infused over 2 minutes following 10-fold dilution with saline (per the package insert).

Figure 8:
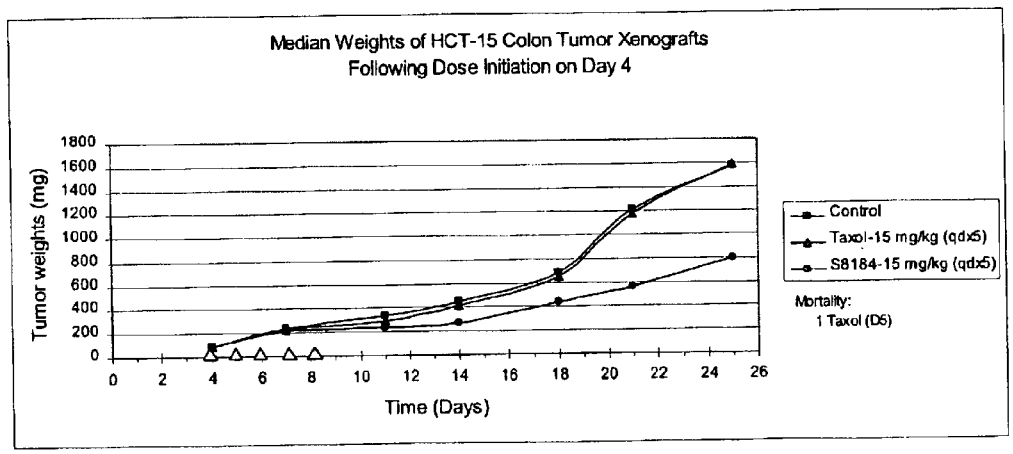
FIG. 8 shows the efficacy of paclitaxel/tocopherol (S8184) and TAXOL in the HCT-15 colon tumor xenograft studies in nude mice.

Preliminary results showed that paclitaxel/tocopherol (S-8184) had significantly higher anti-tumor activity compared with TAXOL, when administered daily for five doses at a dosage of 15 mg/kg/day. In the table, "Vehicle" refers to the tocopherol vehicle. FIG. 8 graphically represents the tumor growth of control, TAXOL-treated and paclitaxel/tocopherol-treated animals.

Example 3

Pharmacokinetics of Paclitaxel After Administration of Taxane/Tocopherol in Humans This example describes pharmacokinetic parameters of a representative paclitaxel/tocopherol composition after bolus administration in humans.

Pharmacokinetic parameters of paclitaxel following 3- and 24-hour infusions of TAXOL at dose levels of 135 mg/m$^2$ and 175 mg/m$^2$ have been previously determined in a Phase 3 randomized study in ovarian cancer patients, as shown in Table 4A in FIG. 9 (see Prescribing Information for TAXOL, available at http://www.bms.com/medicines/data/). The maximum blood concentration ($C_{max}$) of paclitaxel after administration of TAXOL at a dosage level of 175 mg/m$^2$ was 3650 ng/mL.

The pharmacokinetics of paclitaxel/tocopherol was studied in patients with advanced solid malignancies. Dose levels of 175 mg/m$^2$, 200 mg/m$^2$, and 225 mg/m$^2$ of the paclitaxel/tocopherol formulation were administered by an intravenously push through free flowing saline at 3 ml/min to 10 patients at each dose. The concentration of paclitaxel in the formulation was between about 9 and about 10 mg/mL.

A whole blood liquid chromatography/mass spectrometry/mass spectrometry (LC/MS/MS) assay was developed and validated for measurement of paclitaxel levels following paclitaxel/tocopherol administration. The validated range for the assay is 1–200,000 ng/mL. Note that this assay measures paclitaxel in whole blood, including albumin-bound, red blood cell-bound, and free paclitaxel. Therefore, this assay is different from the plasma assay used to study the pharmacokinetics of TAXOL. However, it has been shown that plasma and whole blood assays of paclitaxel after TAXOL administration are similar (Sparreboom et al. (1999) *Cancer Res.* 59(7): 1454–7).

Compared with published data for infusions of TAXOL, the whole blood paclitaxel assay after administration of paclitaxel/tocopherol shows high $C_{max}$, high AUC, low clearance, and long elimination half-life. For example, compared to 3-hour 175 mg/m$^2$ TAXOL infusion, the 175 mg/m$^2$ paclitaxel/tocopherol cohort showed a $C_{max}$ 18-fold higher, $AUC_{0-}$ is 4-fold higher, and clearance is 4 times slower, as shown in Table 4B in FIG. 9. Even higher maximum blood concentrations are obtained by administering the paclitaxel/tocopherol formulation at dosage levels of 200 mg/m$^2$ (77048 ng/mL) and 225 mg/m$^2$ (84012 ng/mL), both of which exceed the maximum recommended dosage level for TAXOL.

The published elimination half-life estimates for 175–180 mg/m$^2$ TAXOL infusions are quite variable. After a 1 hour infusion of TAXOL, the elimination half-life was reported to be 3.3 hours (Mross et al. (2000) *Cancer Chemother. Pharmacol.* 45(6):463–70). After a 3 hour infusion, it was reported to be 13.7 hours (see Ohtsu et al. (1995) *Clin. Cancer. Res.* 1(6):599–606) and 11.1 hours (Chao et al. (1998) *Br. J. Cancer* 78(1):34–39). After 6 hour and 24 hour infusions of TAXOL, the elimination half-life was reported to be 8.6 hours and 13.1 hours, respectively (Wiernik et al. (1987) *Cancer Res.* 47(9):2486–93; Ohtsu et al. 1995, supra). In all these examples, the elimination half-life is substantially shorter than the elimination half-life of 21.5 hours after administration of paclitaxel/tocopherol at a dose of 175 mg/m$^2$. Without limiting the invention to any particular theory of operation, it is possible that the longer elimination half-life of paclitaxel/tocopherol is due to P-glycoprotein inhibition by a component in the formulation, resulting in enhanced tissue absorption, decreased counter transport out of tissues, and decreased clearance (see Sokol et al. (1991) *Lancet* 338(8761):212–4; Boudreaux et al. (1993) *Transplant. Proc.* 24(2):1875; Dintaman et al. (1999) *Pharm. Res.* 16(10):1550–6; Chang et al. (1996) *Clin. Pharmacol. Ther.* 59(3):297–303).

Figure 10:
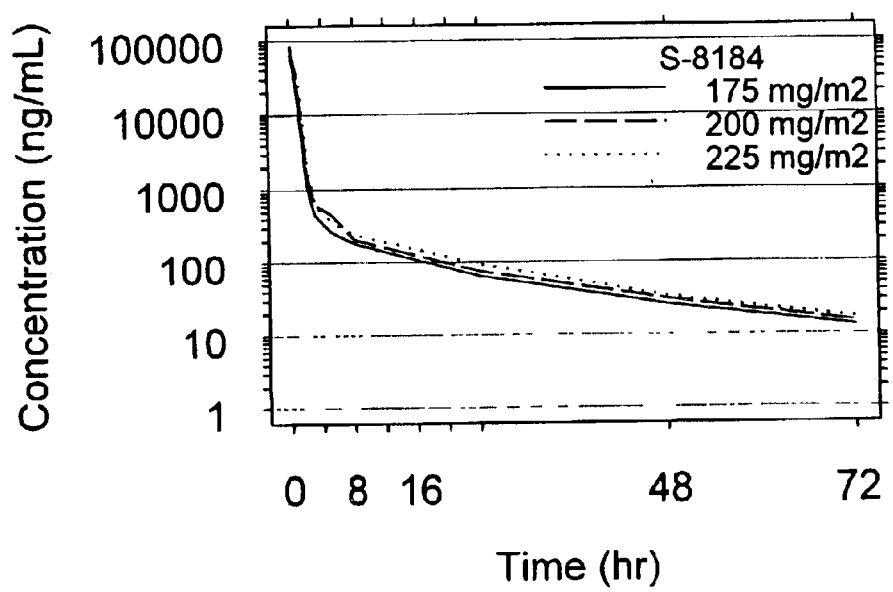
FIG. 10 shows the $C_{max}$, the rapid distribution, and the long terminal elimination half-life after various doses of paclitaxel/tocopherol (S-8184) administration to cancer patients.

The high $C_{max}$, the rapid distribution, and the long terminal elimination half-life for the highest cohorts to date are graphically represented in FIG. 10. The data for this figure represents an average of all patients at the specified dose. FIG. 11 shows that both the AUC and the $C_{max}$ are linearly related to the dose of paclitaxel/tocopherol administered.

Example 4

Tumor Distribution of Paclitaxel After Single Dose of Taxane/Tocopherol

This example shows the comparative tumor paclitaxel biodistribution after administration of a representative paclitaxel/tocopherol composition and TAXOL in B6D2F1 mice subcutaneously implanted with B16 melanoma cells.

Female B6D2F1 mice were subcutaneously implanted with approximately 10$^7$ B16 melanoma cells. Animals were randomized based on bodyweight and tumor size. Paclitaxel/tocopherol emulsion or TAXOL were diluted to final concentrations of 0.6 mg/mL with saline and administered as a bolus (slow push) at a dose of 10 mg paclitaxel/kg bodyweight (17 mL/kg). At predetermined time points of 0.5, 1, 4, 24, 48 and 168 hours after administration, animals were sacrificed and primary tumors were collected for paclitaxel analysis. Tumors were homogenized and analyzed by LC/MS/MS for paclitaxel concentration.

Figure 13:
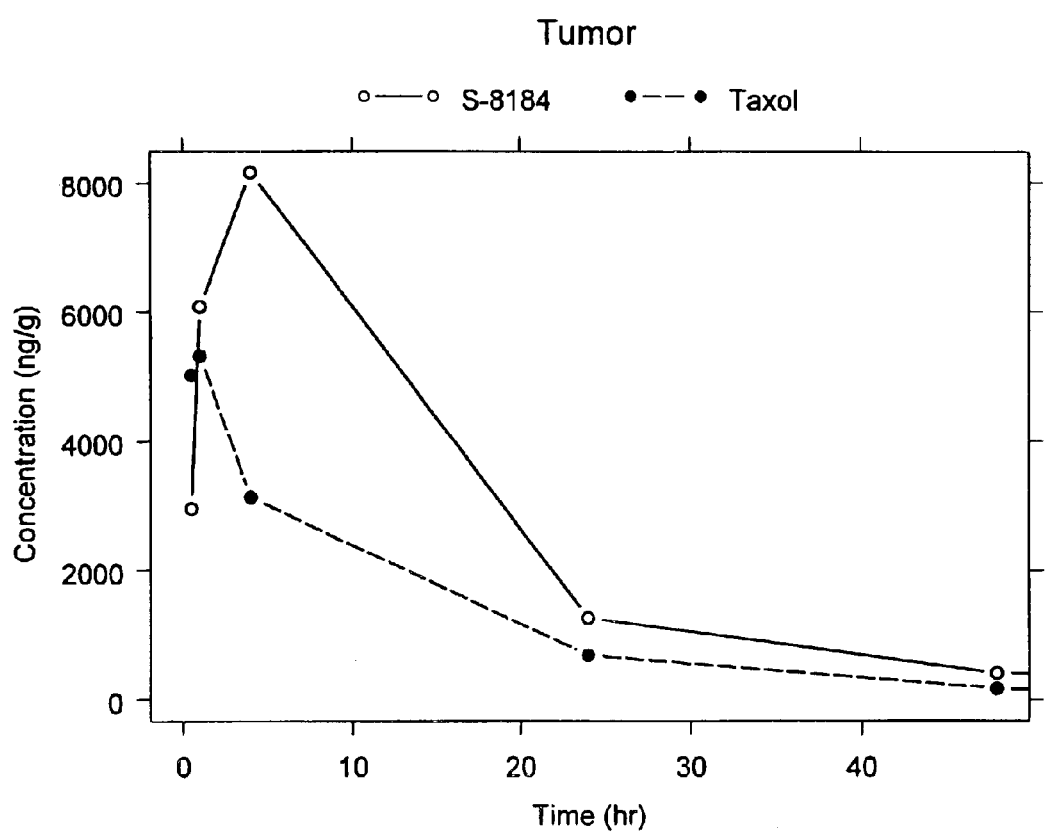
FIG. 13 shows the mean tissue distribution of paclitaxel tumor tissue after intravenous administration of paclitaxel/tocopherol (S-8184) and TAXOL (10 mg paclitaxel/kg.)

The tumor levels of paclitaxel, as determined at several time points after intravenous administration of paclitaxel/tocopherol (S-8184) or TAXOL at a dose of 10 mg/kg are listed in Table 5 in FIG. 12. The calculated pharmokinetic parameters of paclitaxel in tumors are shown in Table 6 in FIG. 12. A significant difference in paclitaxel concentration between the two formulations was observed in tumors. Intravenous administration of paclitaxel/tocopherol into mice bearing B16 melanoma tumors resulted in a higher peak tumor concentration of paclitaxel ($C_{max}$) and a higher AUC in tumors than in animals administered TAXOL. The paclitaxel concentration peaked at 1 hour following TAXOL administration, while the peak occurred at 4 hours following paclitaxel/tocopherol administration. The mean paclitaxel concentration curve for tumor tissues are presented in FIG. 13. From 4 to 48 hours post administration with paclitaxel/tocopherol, the mean paclitaxel tumor concentration was approximately 2-times higher than the tumor concentration of TAXOL treated animals. The higher tumor paclitaxel concentration and AUC following paclitaxel/tocopherol may be the reason for the observed increase in anti-tumor effect of paclitaxel/tocopherol compared to TAXOL observed in -this animal model.

Example 5

Toxicity of Taxane/Tocopherol in Humans

This example describes the evaluation of toxicity and efficacy of a representative paclitaxel/tocopherol compositions administered to humans suffering from solid tumor lesions.

Thirty-seven cancer patients were enrolled in a Phase 1 study of the safety and efficacy of paclitaxel/tocopherol. The following dose levels were explored for paclitaxel/tocopherol: 25, 50, 82.5, 125, 175, 200, and 225 mg/m$^2$. The concentration of paclitaxel in the formulation was between about 9 mg/mL and about 10 mg/mL. Each dose was administered as a bolus injection over 15 minutes. Treatments were repeated every 3 weeks.

The patients suffered from the following tumor types: ovarian (7), colorectal (7), breast (5), non small cell lung (5), mesothelioma (3), pancreas (2), head and neck (2), unknown primary (2), melanoma (1), non-Hodgkins lymphoma (1), sarcoma (1), and small cell lung (1). Nineteen (51%) of the patients had received prior taxane therapy (TAXOL and/or docetaxel). Ten patients were enrolled at each dose of 175, 200, and 225 mg/m$^2$.

The maximum tolerated dose (MTD) was defined as the maximum dose at which fewer than one third of patients among a cohort of a minimum of six patients had a dose limiting toxicity (DLT) during the first dosing cycle (3 weeks). A DLT was defined as any NCI-CTC Grade 4 hematological or Grade 3 non-hematological toxicity. Specific modifications to the NCI-CTC toxicities included: an absolute neutrophil count of less than 500 cells/mm$^3$ for longer than 5 days; a platelet count of less than 25,000/mm$^3$; Grade 2 nausea or vomiting or diarrhea in the presence of maximal prophylaxis; any Grade 4 toxicities or change of more than 2 grades in patients with elevated liver function result; and a treatment delay for more than 2 weeks due to unresolved toxicity and failure to meet criteria for retreatment. In general, a patient must either return to the baseline at which they were enrolled in the study or to a Grade 1 or less non-hematological toxicity prior to subsequent infusion. Adverse events were recorded using the NCI-CTC version 2.0 grading systems (Common Toxicity Criteria Version 2.0, National Cancer Institute, United States National Institutes of Health, revised April 1999) and the MedDRA version 3.3 coding system.

The adverse events described below represent the patient experience for the first 12 patients entered onto the study at doses from 25 mg paclitaxel/m$^2$ to 225 mg/m$^2$. All adverse events are reported, regardless of assigned relationship to the study drug.

The MTD was determined to be 200 mg/m$^2$ of paclitaxel/tocopherol when given as an intravenous push over 10–15 minutes every three weeks. Of 10 patients enrolled at this dose level, one patient had a DLT, grade 4 neutropenia. At the next higher level, 225 mg/m$^2$, in four of ten patients a DLT was observed; grade 4 neutropenia, grade 3 febrile neutropenia, fatigue, and myalgia. No grade 3 or 4 neuropathy was observed at or below the MTD dose of 200 mg/m$^2$.

Other grade 3 non-hematologic toxicities included arthralgia, cramping, dyspnea, fatigue, myalgia, pain, allergy, constipation, diarrhea, migraine, nausea/vomiting, and neuropathy. Common side effects less than or equal to grade 2 include: fatigue, alopecia, nausea, anorexia, arthralgia, myalgia, constipation, diarrhea, flushing, neuropathy, vomiting. Transient flushing, shortness of breath, back pain, and myalgias seen in less than 25% of doses. Symptoms resolve rapidly when the dose is interrupted and intravenous diphenhydramine is administered. All patients have been able to complete each dose. Routine antihistamine premedications are now used.

In this phase 1 study, there are 36 evaluable patients. Twenty one patients have continued progressive disease. In 10 patients the disease has stabilized (2–5 months), in two patients there has been a minor response (tumor area decreased by less than 50%), and in three patients there has been a partial response (tumor area decreased by more than 50%), as documented in Table 7 in FIG. 14. Of the three partial responses, one is response of 11+ months in a patient with taxane-refractory non small cell lung carcinoma (NSCLC), a second is a response of 9+ months in a patient with irinotecan-refractory colorectal cancer, and a third is a response of 3+ months comprising a complete disappearance of liver and spleen metastases in a patient with ovarian cancer.

Example 6

Treatment of Colorectal Carcinomas by Administration of Taxane/Tocopherol

This example describes the administration of a representative paclitaxel/tocopherol composition to humans suffering from colorectal adenocarcinoma.

Paclitaxel/tocopherol formulation is administered to patients with a histologic diagnosis of colorectal adenocarcinoma. The concentration of paclitaxel in the formulation is between about 8–10 mg/mL. The cohort dose is between about 15 and about 225 mg/m$^2$, depending on the administration schedule and other factors.

Paclitaxel/tocopherol formulation is administered every three weeks, every two weeks, once a week, weekly, twice weekly, or daily as an intravenous injection over about 15 to about 30 minutes. The appropriate dose of the paclitaxel/tocopherol formulation may be administered to patients either via a catheter inserted into a large arm vein or directly into a central line, if available.

Example 7

Treatment of Other Carcinomas by Administration of Taxane/Tocopherol

This example describes the administration of a representative paclitaxel/tocopherol composition to humans suffering from transitional cell carcinoma of the urethelium, non small cell lung carcinoma, or ovarian cancer or primary peritoneal carcinoma.

Paclitaxel/tocopherol formulation is administered to patients with a histologic diagnosis of transitional cell carcinoma of the urethelium, non small cell lung carcinoma, or ovarian cancer or primary peritoneal carcinoma. The concentration of paclitaxel in the formulation is between about 8–10 mg/mL. The cohort dose is between about 15 and about 225 mg/m$^2$, depending on the administration schedule and other factors.

Paclitaxel/tocopherol formulation is administered every three weeks, every two weeks, once a week, weekly, twice weekly, or daily as an intravenous injection over about 15 to about 30 minutes. The appropriate dose of the paclitaxel/tocopherol formulation may be administered to patients either via a catheter inserted into a large arm vein or directly into a central line, if available.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for treating a subject suffering from a colorectal carcinoma, comprising:
    administering to a subject suffering from a colorectal carcinoma a therapeutically effective amount of a pharmaceutical composition comprising a taxane and a tocopherol.

2. The method of claim 1, wherein the administration provides anti-tumor activity.

3. The method of claim 1, wherein the tumor was taxane-resistant prior to the administration of the composition.

4. The method of claim 1, wherein the composition is administered in less than about 30 minutes.

5. The method of claim 1, wherein the taxane is administered at a dose in the range from about 15 mg/m$^2$ to about 225 mg/m$^2$.

6. The method of claim 1, wherein the taxane is administered at a dose in the range from about 40 mg/m$^2$ to about 120 mg/m$^2$.

7. The method of claim 1, wherein the taxane is administered once every three weeks.

8. The method of claim 1, wherein the taxane is administered once every two weeks.

9. The method of claim 1, wherein the taxane is administered weekly.

10. The method of claim 1, wherein the taxane is administered twice a week.

11. The method of claim 1, wherein the taxane is administered daily.

12. The method of claim 1, wherein the taxane is paclitaxel.

13. The method of claim 12, wherein the concentration of the paclitaxel in the composition is about 10 mg/ml.

14. The method of claim 1, wherein the composition further comprises at least one of a tocopherol polyethylene glycol derivative, polyethylene glycol, or a polyoxypropylene-polyoxyethylene glycol nonionic block co-polymer.

15. A method for treating a subject suffering from a taxane-resistant colorectal carcinoma, comprising:
    administering to a subject suffering from a taxane-resistant colorectal carcinoma a therapeutically effective amount of a pharmaceutical composition comprising a taxane and a tocopherol, wherein the tumor was taxane-resistant prior to the treatment with the composition.

16. The method of claim 15, wherein the composition is administered in less than about 30 minutes.

17. The method of claim 15, wherein the taxane is administered at a dose in the range from about 15 mg/m$^2$ to about 225 mg/m$^2$.

18. The method of claim 15, wherein the taxane is administered at a dose in the range from about 40 mg/m$^2$ to about 120 mg/m$^2$.

19. The method of claim 15, wherein the taxane is administered once every three weeks.

20. The method of claim 15, wherein the taxane is administered once every two weeks.

21. The method of claim 15, wherein the taxane is administered weekly.

22. The method of claim 15, wherein the taxane is administered twice a week.

23. The method of claim 15, wherein the taxane is administered daily.

24. The method of claim 15, wherein the taxane is paclitaxel.

25. The method of claim 24, wherein the concentration of the paclitaxel in the composition is about 10 mg/ml.

26. The method of claim 15, wherein the composition further comprises at least one of a tocopherol polyethylene glycol derivative, polyethylene glycol, or a polyoxypropylene-polyoxyethylene glycol nonionic block co-polymer.

27. A method for treating a subject suffering from a colorectal carcinoma resistant to a paclitaxel composition comprising polyoxyethylated castor oil and ethanol, comprising:
    administering to a subject suffering from a colorectal carcinoma resistant to a paclitaxel composition comprising polyoxyethylated castor oil and ethanol, a therapeutically effective amount of a pharmaceutical composition comprising a taxane and a tocopherol, wherein the tumor was taxane-resistant prior to the treatment with the composition.

28. A method for treating a subject suffering from a colorectal carcinoma, comprising:
    administering to a subject suffering from a colorectal carcinoma a therapeutically effective amount of a pharmaceutical composition comprising paclitaxel, a tocopherol, and a tocopherol polyethylene glycol derivative.

29. The method of claim 28, wherein the administration provides anti-tumor activity.

30. The method of claim 28, wherein the tumor was taxane-resistant prior to the administration of the composition.

31. The method of claim 28, wherein the composition is administered in less than about 30 minutes.

32. The method of claim 28, wherein the paclitaxel is administered at a dose in the range from about 15 mg/m$^2$ to about 225 mg/m$^2$.

33. The method of claim 28, wherein the paclitaxel is administered at a dose in the range from about 40 mg/m$^2$ to about 120 mg/m$^2$.

34. The method of claim 28, wherein the composition is administered once every three weeks.

35. The method of claim 28, wherein the composition is administered once every two weeks.

36. The method of claim 28, wherein the composition is administered weekly.

37. The method of claim 28, wherein the composition is administered twice a week.

38. The method of claim 28, wherein the composition is administered daily.

39. The method of claim 28, wherein the concentration of the paclitaxel in the composition is about 10 mg/ml.

40. The method of claim 28, wherein the composition further comprises at least one of polyethylene glycol, or a polyoxypropylene-polyoxyethylene glycol nonionic block co-polymer.

41. A method for treating a subject suffering from a colorectal carcinoma, comprising:
    administering to a subject suffering from a colorectal carcinoma a therapeutically effective amount of a pharmaceutical composition comprising a taxane; α-tocopherol; a tocopherol polyethylene glycol succinate; and an aqueous phase; wherein the composition is an emulsion or a microemulsion having an oil and a water phase, and wherein all of the taxane is in the oil phase.

42. The method of claim 41, wherein the taxane is paclitaxel.

* * * * *

UNITED STATES PATENT AND TRADEMARK OFFICE
CERTIFICATE OF CORRECTION

PATENT NO. : 6,727,280 B2
DATED : April 27, 2004
INVENTOR(S) : N. Palepu et al.

It is certified that error appears in the above-identified patent and that said Letters Patent is hereby corrected as shown below:

<u>Title page,</u>
Item [60], Related U.S. Application Data, "60/048,480," should read -- 60/048,840, --
Item [56], References Cited, FOREIGN PATENT DOCUMENTS,
"WO 98/30204 A1   2/1997" should be -- WO 98/30204 A1   7/1998 --

Signed and Sealed this

Thirtieth Day of November, 2004

JON W. DUDAS
*Director of the United States Patent and Trademark Office*